United States Patent
Storås et al.

(10) Patent No.: US 11,761,889 B2
(45) Date of Patent: Sep. 19, 2023

(54) GAS DETECTOR

(71) Applicant: Optronics Technology AS, Oslo (NO)

(72) Inventors: Preben Storås, Oslo (NO); Lasse Irvam, Fredrikstad (NO)

(73) Assignee: Optronics Technology AS, Oslo (NO)

( * ) Notice: Subject to any disclaimer, the term of this patent is extended or adjusted under 35 U.S.C. 154(b) by 8 days.

(21) Appl. No.: 17/639,539

(22) PCT Filed: Aug. 12, 2020

(86) PCT No.: PCT/EP2020/072644
§ 371 (c)(1),
(2) Date: Mar. 1, 2022

(87) PCT Pub. No.: WO2021/043555
PCT Pub. Date: Mar. 11, 2021

(65) Prior Publication Data
US 2022/0317039 A1 Oct. 6, 2022

(30) Foreign Application Priority Data
Sep. 2, 2019 (NO) ............................. NO20191052

(51) Int. Cl.
*G01N 21/39* (2006.01)
*G01J 3/26* (2006.01)
(Continued)

(52) U.S. Cl.
CPC ............... *G01N 21/39* (2013.01); *G01J 3/26* (2013.01); *G01N 33/0063* (2013.01); *G08B 21/12* (2013.01); *G08B 21/182* (2013.01)

(58) Field of Classification Search
CPC ............ G01N 21/39; G01N 21/3504; G01N 33/0063; G01N 2021/3513; G01J 3/26; G08B 21/12; G08B 21/182; G08B 17/103
See application file for complete search history.

(56) References Cited

U.S. PATENT DOCUMENTS 5,451,787 A * 9/1995 Taylor .................... G01N 21/39
250/338.5
6,337,741 B1 1/2002 Lind
(Continued)

FOREIGN PATENT DOCUMENTS

DE 102004063667 A1 7/2006
EP 3081922 A1 10/2016
(Continued)

OTHER PUBLICATIONS

Consalvo, Daniela; International Search Report; PCT/EP2020/072644; dated Dec. 1, 2020; 5 pages.

*Primary Examiner* — Tarifur R Chowdhury
*Assistant Examiner* — Carlos Perez-Guzman
(74) *Attorney, Agent, or Firm* — BRADLEY ARANT BOULT CUMMINGS LLP

(57) ABSTRACT

The present invention relates to a gas measuring system for measuring the presence of a predetermined gas including a light source and a light receiver separated by a gas volume, the light source emitting light within a chosen range of wavelengths including characteristic absorption wavelengths of the gas to be measured and the light receiver being capable of detecting light in said wavelength range and the system including a spectrum analyzer and a storage means for storing the specific absorption wavelengths of the gas thus to recognize a gas absorbing at said specific wavelengths. The storage means also includes specific absorption wavelengths characterizing at least one other material having absorption wavelengths partially overlapping the absorption wavelengths of said gas, and thus detect the material in the volume. The system includes an analyzer unit being adapted to detect said other material from the gas measurements so as to distinguish between said material and gas in the volume, and to provide a measure of said gas.

14 Claims, 3 Drawing Sheets

(51) Int. Cl.
  *G01N 33/00* (2006.01)
  *G08B 21/12* (2006.01)
  *G08B 21/18* (2006.01)

(56) References Cited

U.S. PATENT DOCUMENTS

| | | |
|---|---|---|
| 6,509,566 B1 | 1/2003 | Wamsley et al. |
| 9,250,418 B2 | 2/2016 | Bakke et al. |
| 2008/0198027 A1 | 8/2008 | Bugge |
| 2015/0099274 A1 | 4/2015 | Axelrod et al. |
| 2016/0305870 A1* | 10/2016 | Ooyama ............ G01N 33/0047 |

FOREIGN PATENT DOCUMENTS

| | | |
|---|---|---|
| WO | WO-2013109728 A1 | 7/2013 |
| WO | WO-2018001851 A1 | 1/2018 |
| WO | WO-2019117730 A1 | 6/2019 |

\* cited by examiner

GAS DETECTOR

The present invention relates to a gas measuring system for measuring the presence of a predetermined gas under conditions also including other materials. More specifically the present invention relates to open path gas detectors including a light source and detector capable of analyzing the spectrum of the received light.

Gas detectors of different types have been well known for a long time, for example as described in U.S. Pat. No. 6,337,741. The spectrum analysis may be performed by changing the wavelength of the source, e.g. using tunable lasers, or by analyzing the received light from a known source after having passed through the gas volume. Scanning through the wavelengths using optical spectrum analyzers such as Fabry-Perot interferometers is discussed in US2015/099274A1, DE102004063667A1, U.S. Pat. No. 9,250,418B2 and WO2018/001851. In WO2013/109728 a solution is discussed where silicon-containing compounds are detected in a biogas by finding the difference between the biogas/compound mixture and the biogas. A similar solution is also discussed in U.S. Pat. No. 6,509,566.

The present invention is especially aimed at use in in the Oil and Gas industry where gas leaks are feared. Natural gas and biogas consist of both explosive and toxic gases, and Methane Detectors or general Hydrocarbon Detectors are used to detect leaks or releases before they reach an explosive concentration.

Two types of Optical Gas detectors dominate: Point Gas Detectors and Open Path Detectors. Point Detectors measures the gas that reaches the detection point of the detector and must therefore be close to the leak point, and positioned correct relative to the wind direction. Open Path Detectors consists of one unit that is emitting light and another unit that measures the light, and these two units can be placed far from each other so that the light beam passes through the monitored area. These two units can detect gases passing between them. This way, large areas can be "fenced" in with a few Open Path detectors effectively monitoring for gas. Using Point Detectors to monitor such an area would in many situations demand too many detectors. In theory Open Path should be more suitable for such areas, but in reality they are not used due to the danger of false positives resulting in false alarms and possibly automatic shutdown of the installation where the detector is positioned, with resulting loss of production.

It is therefore an object of the present invention to provide a gas detector system capable of eliminating or reducing the danger of false alarms in a open path gas sensors. This is obtained with a system as described above and characterized as presented in the accompanying claims.

The present invention is thus based on the realization that false alarms may be caused by plastic material being brought into the optical path that can trigger an alarm, for example a plastic bag or plastic particles, in the beam path of the gas sensor. The challenge with plastic is that the material it is made from Hydrocarbon molecules, and basically the same as is detected by existing optical hydrocarbon gas detectors. In the optical spectrum plastic and hydrocarbon gas absorption spectra are similar and therefore open path detectors where the light beam passes through the material brought into the light beam are highly susceptible to any plastic material that is passing by as the sensor will detect absorption in the light transmitted through the plastic corresponding to the expected absorption in the gas.

As the occurrence of a plastic material in the sensor area may occur suddenly and for a short period of time it is also an object of the invention to evaluate and decide if there is a gas detection or an intruding plastic detection within a specific time period which in hydrocarbon installations often is in the range of 5 seconds.

The invention will be described more in detail below with reference to the accompanying drawings, illustrating the invention by way of examples.

Figure 1A:
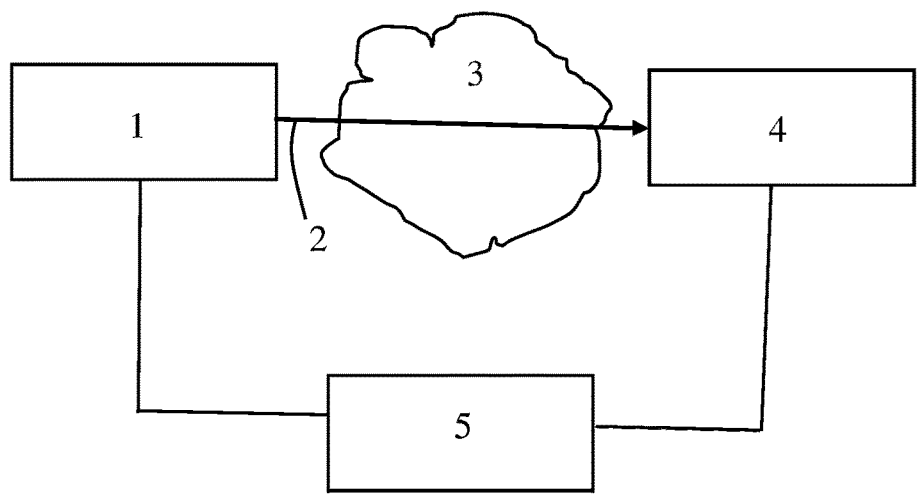
FIG. 1a, 1b illustrates typical constructions of an open path detector.

In general, an open path gas detection system consists of at least two modules as illustrated in FIG. 1a, one transmitter module 1 (transmitter) and one receiver module 4 (receiver). The transmitter contains a light source transmitting a light beam 2 toward the receiver through the gas volume 3 to be monitored. The receiver 4 contains a sensor that measures the light 2 coming from the transmitter 1. Gas molecules 3 between the transmitter 1 and receiver 4 will absorb at specific wavelengths of the light sent from the transmitter to the receiver, and the optical path length may typically be in the range from 50 cm. From the amount of light lost between transmitter and receiver the amount of gas molecules in the light beam can be calculated in a computer module 5 being connected to both transmitter 1 and receiver 5. The computer model 5 may be positioned in direct contact with the transmitter 1 and/or receiver 4 or being in another position communicating through wireless or wired connections.

Figure 1B:
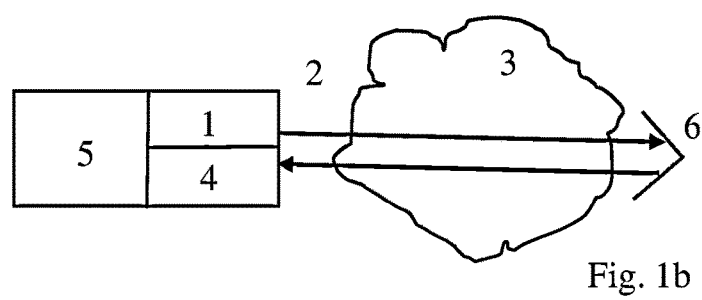

As is illustrated in FIG. 1b the transmitter 1 and receiver 4 may be positioned in the same unit using a mirror 6 reflecting the light beam back toward the unit. This unit may also include the computer module 5.

For open path systems typically two wavelengths are sent from the transmitter to the receiver, one that is absorbed by the gas and one that is not absorbed. The difference between these two wavelengths is a measure on the amount of gas. Plastic consists of molecule chains built up of the same molecules as the gas to be measured, and therefore is absorbing at the same wavelength as the gas to be detected. But since the plastic is a solid with longer molecule chains there are some distinct differences in the absorption spectrum that can be found if you scan larger parts of the spectrum and analyses this. The present invention relates to a method to distinguish a real gas measurement from a false detection from plastic.

Figure 1C:
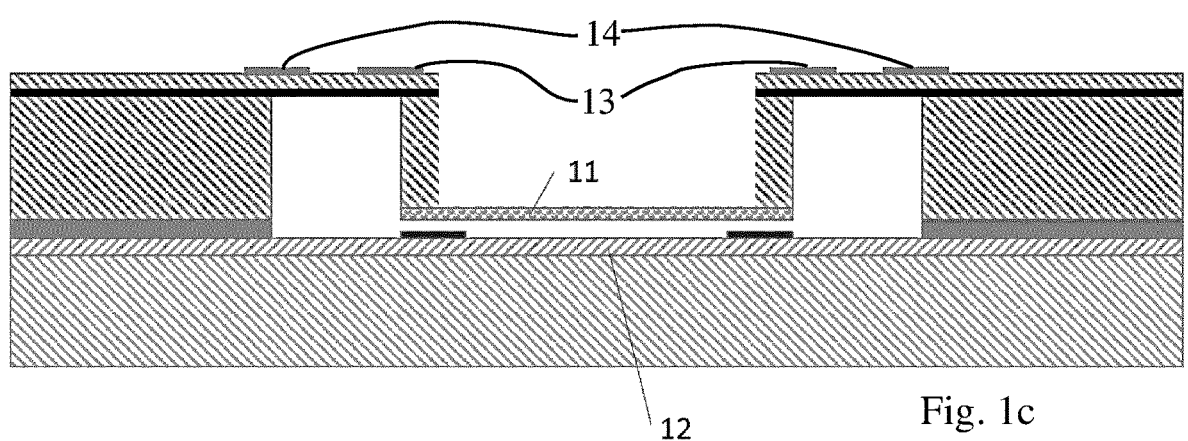
FIG. 1c illustrates an interferometer used according to a preferred embodiment of the invention.

To separate out a false Gas detection from plastic and not risking the Safety by not alarming when there is a real gas leak, requires good data of the optical spectrum combined with a method with very high confidence. Basically, an Optical Spectrum analyzer is required. For an Open Path system there are several restriction limiting what solution that can be used. The Spectrum Analyzer would often need to be very compact, operate in a wide temperature range, being robust to vibration, long lifetime and there should preferably be no moving parts. This may preferably be obtained using the adjustable Fabry-Perot interferometers such as illustrated in FIG. 1c and discussed in abovementioned U.S. Pat. No. 9,250,418B2 and especially WO2018/001851, thus providing robust scanning over a wavelength range sufficiently large to incorporate the typical spectra of the plastic and gas. Depending on the situation the interferometer may be positioned in the transmitter part 1, controlling the light sent into the gas, or the receiver part 4, scanning through the light received from the gas, but preferably it is positioned in relation to the receiver and analyzer. These interferometers are also sufficiently fast to measure within a relevant volume within a time frame small enough not to have significant changes in the gas volume and within the predetermined time required between a detected possible gas occurrence and an alarm or shut-down, such as 5 seconds. The interferometers are capable of scanning through wide range of wavelengths by using two sets of actuators 13,14 to change the distance between the mirrors 11,12, as illustrated in FIG. 1c. In WO2018/001851 the two actuators are used as two scanning frequencies, where one is a slow, wide range scanning and the second is a fast short-range scanning.

According to a preferred embodiment the predetermined wavelength is scanned a number of times in order to increase the quality of the measurements and then evaluated by the spectrum analyzer before deciding to indicate the presence of a gas. The scanning frequency may be from 100 Hz to several kHz depending on the scanned range and the method used, e.g. if the filter moves between specific wavelengths or scans over the complete range. This requires both accurate and fast scanning capabilities, which may be obtained by the use of interferometers of the type mentioned above.

The method would consist of software algorithms developed from analysis of plastic spectrums compared with gas spectrums, and other effects affecting real applications. The applications where a Spectrum Analyzer with Safe algorithms is used in Open Path systems to avoid False positive Gas detections are hereby patented.

Figure 2:
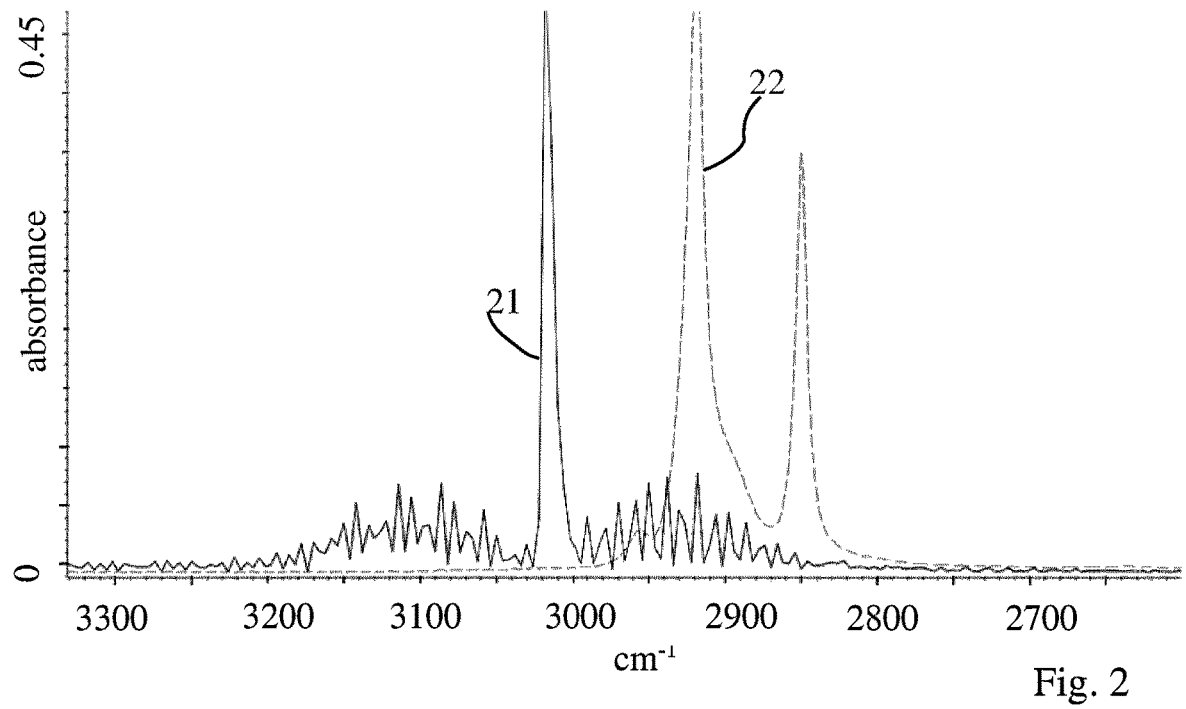
FIGS. 2 and 3 illustrates a typical spectrum of methane compared with the spectrum of polyethylene plastic.

FIG. 2 illustrates an example of a typical plastic that can interfere with the gas measurement of Methane gas, methane gas in black color 21 and Polyethylene (PE) plastic in dotted line 22. In this case the gas is measured at around 3000 $cm^{-1}$, and since the plastic spectrum is overlapping Methane it will trigger false alarm, especially if the measurements are not capable of distinguish the close peaks 21, 22 at 3010 and 2920 $cm^{-1}$. By doing a detailed scan of the spectrum with a high finesse interferometer, within the range 2000-5000 $cm^{-1}$ (wavelength of 2-5 μm) the shape can be used to distinguish between the plastic and gas. This may for example be done by comparing the response at 3010 $cm^{-1}$ with 2920 $cm^{-1}$ and 2840 $cm^{-1}$ or, for example if the wavelength resolution of the filter is insufficient analyzing the scanned continuous shape of the spectrum over a selected range to find deviations in the shape form the expected spectrum and the measured spectrum. This way false alarms may be avoided by recognizing when it is plastic and not a gas detection. Using the Fabry-Perot filter illustrated in FIG. 1c, this can for example be done by scanning within the range covering these three peaks or just the 3010 $cm^{-1}$ with 2920 $cm^{-1}$ absorption peaks 21,22.

Figure 3:
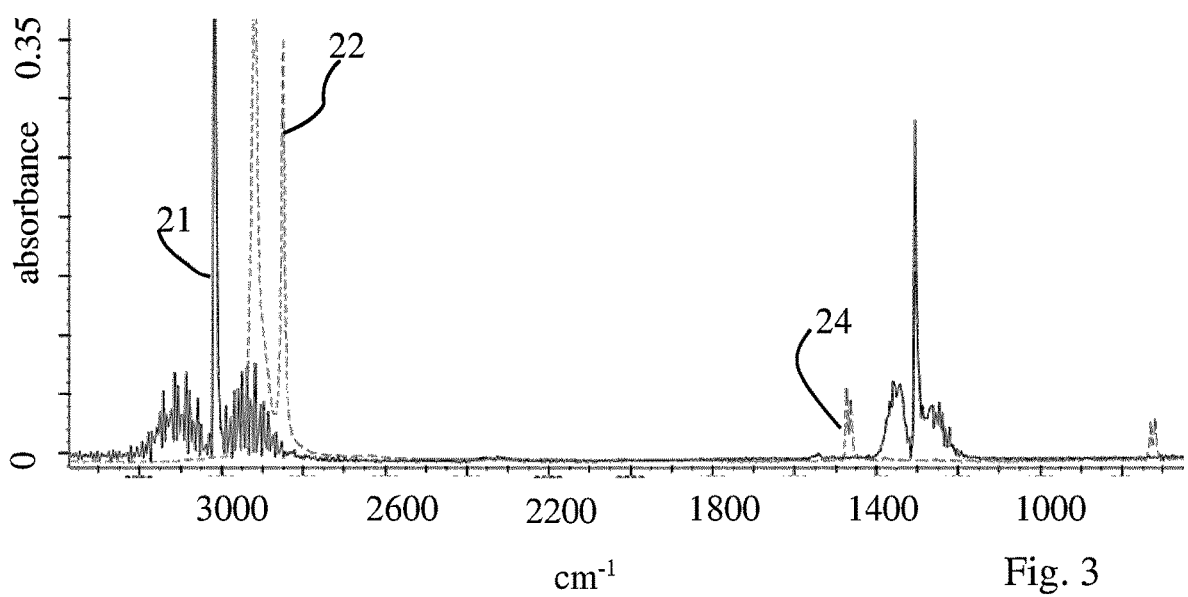

In addition to recognizing the plastic by the shape of the spectrum as illustrated in FIG. 2, it can be recognized that it is located in several specific places in the spectrum as illustrated in FIG. 3, where the peak 24 at 1470 $cm^{-1}$ can provide a measure of the plastic present in the measured volume if the range of measured wavelengths is set to 1000-3500 $cm^{-1}$.

Figure 4:
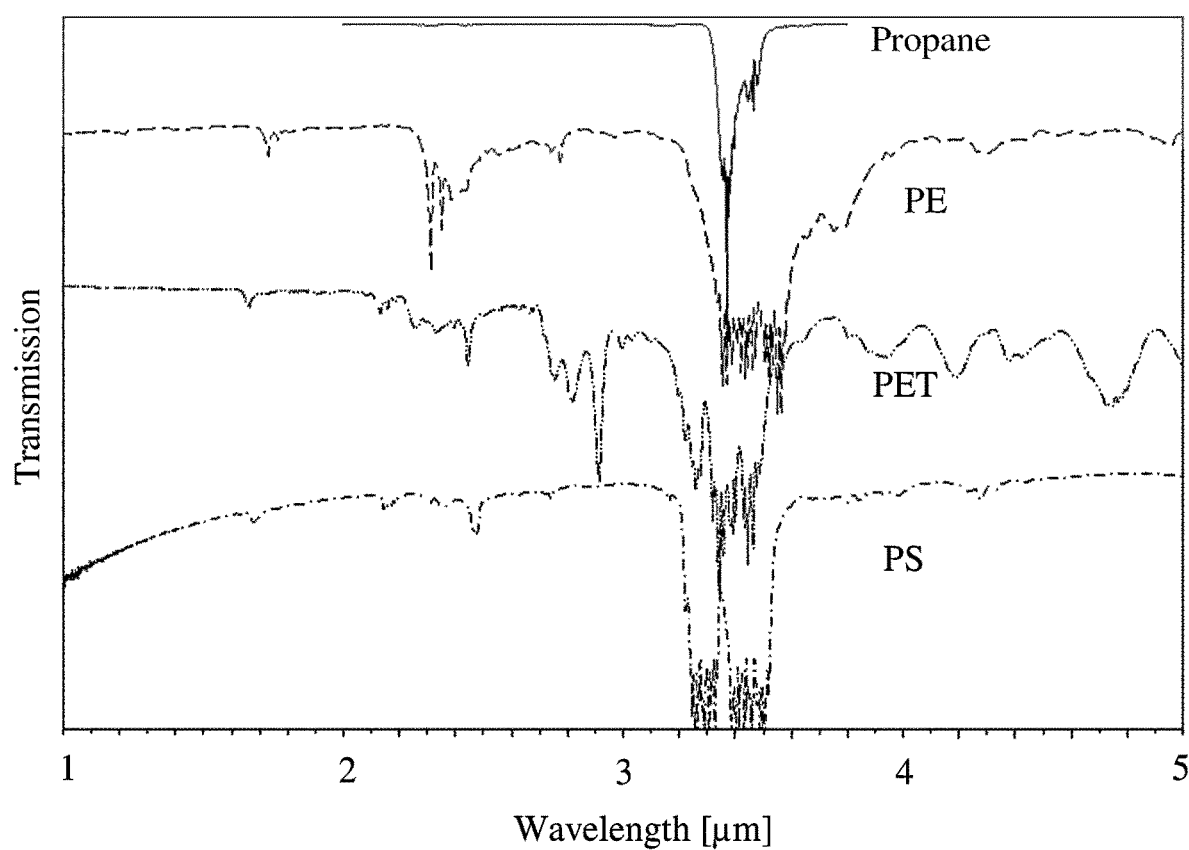
FIG. 4 shows a propane transmission spectrum compared with plastic materials PE, PET, and PS.

FIG. 4 shows a comparison optical transmission spectra of Propane gas with different plastics. The plots shows how three different plastic materials (PE, PET, PS) are absorbing at the same wavelengths as Propane and thereby triggering a false alarm. It can also be clearly seen that the plastic has distinctly different spectra than the gas and can therefore be recognized and reported as a false gas detection, thus scanning through the spectrum it will be possible to compare the measured spectrum with the stored spectra deciding whether the gas or a plastic material is present in the light path as the width and shape of the spectrum differs.

Thus, the present invention is related to a gas measuring system or a related method where the characteristic spectrum or wavelengths of one or more plastic materials is monitored at the same time, or sequentially through scanning at a sufficiently high rate, with the characteristic spectrum or wavelengths of the monitored gas, where at least part of the two characteristic spectra or wavelength sets do not overlap. If a significant amount of the plastic material is detected the gas detection may be considered to be uncertain and a warning signal generated, or the system may enter a processing phase subtracting the signal caused by the plastic from the gas signal to maintain a sufficiently accurate gas measurement.

The thresholds chosen for defining the detection of a gas or plastic detection may depend on the situation and the gas or plastic type. As one object of the invention is to avoid false alarmed triggered by plastic material entering the measured volume the chosen wavelengths characterizing the plastic may be chosen so as to indicate the presence of different types of plastic, e.g. in wavelength ranges the plastic types have in common.

To summarize the present invention relates to a gas measuring system for measuring the presence of a predetermined gas including a light source and a light receiver separated by a gas volume. The light source emits light within a chosen range of wavelengths including characteristic absorption wavelengths of the gas to be measured and the light receiver is suitable for detecting light in said wavelength range. The system includes a spectrum analyzer and a storage means for storing the specific absorption wavelengths of the gas in order to be able to compare measured values with the stored values and recognize a gas absorbing at said specific wavelengths.

The storage means also includes specific absorption wavelengths characterizing at least one other material having absorption wavelengths partially overlapping the absorption wavelengths of said gas and therefore the differences between the other material and the measured gas to be able to detect the material in the measured gas volume, the other material including a plastic material.

The system including an analyzer unit including a spectrum analyzer and computer device, being adapted to subtract the detected other material from the gas measurements so as to distinguish between said material and gas in the volume and send an alarm when the measure of the gas is above a certain threshold and no other materials are present, or the known absorption of the other material in the wavelengths in which the gas is measured is subtracted from the signal so as to adjust the measured amount of gas before comparing the amount with the threshold before triggering an alarm signal. The threshold for triggering the alarm will depend on the individual gas according to known regulations.

The gas may be a hydrocarbon gas of the types Methane, or Propane, or Ethylene, or Butane, or CO2, while plastic material is constituted by plastic particles and/or objects in the light path having known spectra, where the plastic may be of the types polyethylene (PE), PVC, polyethylene Teraphthalate (PET) polystyrene (PS) or polycarbonate.

The wavelength range used will depend on the gas type but is in the range of is 2-5 μm, typically for short distances in the range of 2.8-4.9 μm. Because of the absorption in the air the range for longer light paths will typically be 2-3 µm for methane and 3.2-3.6 for propane, as can be seen for the illustrated spectra.

The light source may be a laser adapted to scan over the wavelength range, the spectrum analyzer being adapted to compare the timing of the emitted light and intensity of the received light, but will preferably be based on a broadband light source covering the intended range and a light receiver including a scanning Fabry Perot interferometer, which is adapted to scan over the chosen wavelength range. The spectrum analyzer being adapted to compare the timing of the scanning Fabry Perot wavelength with the intensity of the received light.

Typically the gas detection unit used for measuring flammable gases like methane is encapsulated inside an Explosion proof container so it is suitable for installation in a hazardous area such as an Ex zone with flammable gases, liquids or dust without significant risk of igniting the beforehand mentioned flammable substances even if there is an ignition or explosion inside the container.

The invention claimed is:

1. A gas measuring system for measuring the presence of a predetermined gas, comprising:
   a light source and a light receiver separated by a gas volume, the light source emitting light within a chosen range of wavelengths including characteristic absorption wavelengths of the gas to be measured, the light receiver for detecting light in the wavelength range;
   a spectrum analyzer;
   wherein specific absorption wavelengths of the gas are stored in order to recognize a gas absorbing at the specific wavelengths;
   wherein the stored specific absorption wavelengths comprise at least one other material, the other material being constituted by plastic particles or plastic objects having absorption wavelengths partially overlapping the absorption wavelengths of the gas within the chosen range of wavelengths; and
   an analyzer unit adapted to detect the other material based on the specific absorption wavelengths of the other material in the gas measurements so as to distinguish between the other material and the gas in the volume from the differences between the absorption wavelengths and to provide a measurement of the gas.

2. The gas measuring system according to claim 1, wherein the gas measuring system is adapted to provide a measurement of the gas when the detected amount of the other material is below a predetermined threshold and to trigger an alarm when the detected mount is above a predetermined threshold.

3. The gas measuring system according to claim 1, wherein the analyzer unit provides the measurement of the gas by subtracting the influence of the detected other material from the measured at the specific wavelengths of the gas and is adapted to trigger an alarm when the measurement is above a predetermined threshold.

4. The gas measuring system according to claim 1, wherein the gas is a hydrocarbon gas.

5. The gas measuring system according to claim 1, wherein the plastic particles or plastic objects is made from at least one of PVC, PET, PS, PE, and polycarbonate.

6. The gas measuring system according to claim 1, wherein the volume is position in line of the light beam between the source and the receiver.

7. The gas measuring system according to claim 6, comprising a retroreflective element in the direction of the light beam, the source and emitter being in the same unit and the volume being between the unit and the reflector.

8. The gas measuring system according to claim 6, wherein the optical distance between the source and the receiver is at least 50 cm.

9. The gas measuring system according to claim 1, wherein the wavelength range is 2-5 µm.

10. The gas measuring system according to claim 1, wherein the light source is a laser adapted to scan over the wavelength range, the spectrum analyzer being adapted to compare the timing of the emitted light and intensity of the received light.

11. The gas measuring system according to claim 1, wherein the light source emits light within the range and the light receiver is a scanning Fabry Perot interferometer, adapted to scan over the wavelength range, the spectrum analyzer being adapted to compare the timing of the scanning Fabry Perot wavelength with the intensity of the received light.

12. The gas measuring system according to claim 1, encapsulated inside an explosion proof container, so as to be suitable for installation in a hazardous area.

13. The gas measuring system according to claim 4, wherein the hydrocarbon gas is a gas selected from the group consisting of Methane, Propane, Ethylene, and Butane.

14. The gas measuring system according to claim 12, wherein the hazardous area has at least one of flammable gases, explosive gases, liquids, and dust.

* * * * *